US012753244B2

(12) United States Patent
Sung

(10) Patent No.: US 12,753,244 B2
(45) Date of Patent: Oct. 6, 2026

(54) MONOCLONAL ANTIBODY USED FOR DIAGNOSIS AND EARLY ONSET OF PROSTATE CANCER

(71) Applicant: Taipei Medical University, New Taipei City (TW)

(72) Inventor: Shian-Ying Sung, Stockton, CA (US)

(73) Assignee: TAIPEI MEDICAL UNIVERSITY, New Taipei City (TW)

( * ) Notice: Subject to any disclaimer, the term of this patent is extended or adjusted under 35 U.S.C. 154(b) by 0 days.

(21) Appl. No.: 18/992,587

(22) PCT Filed: Sep. 27, 2023

(86) PCT No.: PCT/US2023/075190
§ 371 (c)(1),
(2) Date: Jan. 9, 2025

(87) PCT Pub. No.: WO2024/073460
PCT Pub. Date: Apr. 4, 2024

(65) Prior Publication Data

US 2025/0263501 A1 Aug. 21, 2025

Related U.S. Application Data

(60) Provisional application No. 63/377,801, filed on Sep. 30, 2022.

(51) Int. Cl.
*C07K 16/28* (2006.01)
*A61K 47/68* (2017.01)
*A61P 35/00* (2006.01)
*G01N 33/57555* (2026.01)

(52) U.S. Cl.
CPC ...... *C07K 16/2896* (2013.01); *A61K 47/6869* (2017.08); *A61P 35/00* (2018.01); *G01N 33/57555* (2026.01); *C07K 2317/565* (2013.01); *C07K 2317/76* (2013.01); *G01N 2333/70596* (2013.01)

(58) Field of Classification Search
CPC .......... C07K 16/2896; C07K 2317/565; C07K 2317/76; C07K 16/3069; A61K 47/6869; A61P 35/00; G01N 33/57555; G01N 2333/70596
See application file for complete search history.

(56) References Cited

U.S. PATENT DOCUMENTS

2011/0076284 A1 3/2011 Corbin et al.
2021/0077482 A1 3/2021 Chari et al.

FOREIGN PATENT DOCUMENTS

WO 2019075300 A2 4/2019

*Primary Examiner* — Nelson B Moseley, II
(74) *Attorney, Agent, or Firm* — Lisa Mueller; Casimir Jones SC

(57) ABSTRACT

The present invention provides a monoclonal antibody designed for the diagnosis and early detection of prostate cancer, particularly in relation to a monoclonal antibody developed to target the specificity of soluble ADAM9 variants (sADAM9v2) secreted in the vicinity of prostate cancer.

12 Claims, 5 Drawing Sheets

Specification includes a Sequence Listing.

SEQUENCE LISTING

```
Sequence total quantity: 10
SEQ ID NO: 1            moltype = AA  length = 8
FEATURE                 Location/Qualifiers
source                  1..8
                        mol_type = protein
                        organism = Homo sapiens
SEQUENCE: 1
GYTFTSYD                                                            8

SEQ ID NO: 2            moltype = AA  length = 8
FEATURE                 Location/Qualifiers
source                  1..8
                        mol_type = protein
                        organism = Homo sapiens
SEQUENCE: 2
IYPRDGST                                                            8

SEQ ID NO: 3            moltype = AA  length = 7
FEATURE                 Location/Qualifiers
source                  1..7
```

-continued

```
                        mol_type = protein
                        organism = Homo sapiens
SEQUENCE: 3
ARWGGDH                                                       7

SEQ ID NO: 4            moltype = AA  length = 12
FEATURE                 Location/Qualifiers
source                  1..12
                        mol_type = protein
                        organism = Homo sapiens
SEQUENCE: 4
QSLLNSRTRK NY                                                 12

SEQ ID NO: 5            moltype =   length =
SEQUENCE: 5
000

SEQ ID NO: 6            moltype = AA  length = 8
FEATURE                 Location/Qualifiers
source                  1..8
                        mol_type = protein
                        organism = Homo sapiens
SEQUENCE: 6
KQSYILWT                                                      8

SEQ ID NO: 7            moltype = AA  length = 102
FEATURE                 Location/Qualifiers
source                  1..102
                        mol_type = protein
                        organism = Homo sapiens
SEQUENCE: 7
VQLEQSGPEL VKPGASVKLS CKASGYTFTS YDINWVRQRP GQGLEWIGWI YPRDGSTTFN  60
EKFRGKARLT VDTSSSTAYM ELHSLTSEDS AVYFCARWGG DH                    102

SEQ ID NO: 8            moltype = AA  length = 100
FEATURE                 Location/Qualifiers
source                  1..100
                        mol_type = protein
                        organism = Homo sapiens
SEQUENCE: 8
VLTQSPSSLA VSAGEKVTMS CKSSQSLLNS RTRKNYLAWY QQKPGQSPKR LIYWASTRES  60
GVPDRFTGSG SGTDFTLTIS SVQTEDLAVY YCKQSYILWT                      100

SEQ ID NO: 9            moltype = AA  length = 114
FEATURE                 Location/Qualifiers
source                  1..114
                        mol_type = protein
                        organism = Homo sapiens
SEQUENCE: 9
DVQLEQSGPE LVKPGASVKL SCKASGYTFT SYDINWVRQR PGQGLEWIGW IYPRDGSTTF  60
NEKFRGKARL TVDTSSSTAY MELHSLTSED SAVYFCARWG GDHWGQGTTL TVSS        114

SEQ ID NO: 10           moltype = AA  length = 114
FEATURE                 Location/Qualifiers
source                  1..114
                        mol_type = protein
                        organism = Homo sapiens
SEQUENCE: 10
SSELVLTQSP SSLAVSAGEK VTMSCKSSQS LLNSRTRKNY LAWYQQKPGQ SPKRLIYWAS  60
TRESGVPDRF TGSGSGTDFT LTISSVQTED LAVYYCKQSY ILWTFGGGTK LEIK        114
```

MONOCLONAL ANTIBODY USED FOR DIAGNOSIS AND EARLY ONSET OF PROSTATE CANCER

CROSS-REFERENCE TO RELATED APPLICATIONS

This application is a national stage application of PCT/US2023/075190, filed Sep. 27, 2023, which claims the priority of U.S. Provisional Patent Applications 63/377,801 filed on Sep. 30, 2022. The entirety of the aforementioned application is incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 9,477 Byte XML file named "24P0841_final.xml," created on Jan. 26, 2026.

FIELD OF THE INVENTION

The present disclosure pertains to a monoclonal antibody designed for the diagnosis and early detection of prostate cancer, particularly in relation to a monoclonal antibody developed to target the specificity of soluble ADAM9 variants secreted in the vicinity of prostate cancer.

BACKGROUND OF THE INVENTION

Based on the 2021 national cancer registry data from Taiwan, prostate cancer holds the sixth position in terms of incidence among Taiwanese men and stands fifth in mortality rates. Notably, the early manifestations of prostate cancer are usually subtle and resemble those of prostate hyperplasia, leading to potential oversight. It is only when prostate cancer infiltrates seminal vesicles, manifesting symptoms like hematospermia or painful ejaculation, or metastasizes to other organs, that it garners significant attention.

Therefore, an efficacious methodology tor the early detection of prostate cancer is of paramount importance.

SUMMARY OF THE INVENTION

ADAM9 has been shown to increase its expression in numerous cancer epithelial cells, such as prostate, breast, kidney, and lung cancers. The enhanced expression has been positively correlated with cancer progression and metastasis tendencies. Research indicates that the predominant protein expression could be attributable to soluble ADAM9 (sADAM9).

Concurrently, two distinct splice variants of sADAM9 have been identified, including sADAM9v1, reported by Mazzocca et al, and sADAM9v2, a novel variant identified by the inventors of the present application. It is pivotal to highlight that sADAM9v2 is expressed not only by malignant prostate cancer cells but also in the surrounding cells proximal to the prostate cancer.

Hereinafter, the present disclosure provides an antibody or antigen-binding fragment thereof that binds to a sADAM9v2 protein or a segment of its peptide. This antibody or its antigen-binding fragment is characterized by: a heavy chain that encompasses CDR1 with an amino acid sequence of SEQ ID NO: 1, CDR2 with an amino acid sequence of SEQ ID NO: 2, and CDR3 with an amino acid sequence of SEQ ID NO: 3; in tandem with a light chain that contains CDR1 with an amino acid sequence of SEQ ID NO: 4, CDR2 with an amino acid sequence of SEQ ID NO: 5, and CDR3 with an amino acid sequence of SEQ ID NO: 6.

Preferably, the antibody or antigen-binding fragment comprises: a heavy chain variable region comprising the amino acid sequence having at least 70%, preferably at least 80%, or more preferably at least 90%, identity to SEQ ID NO: 7; and alight chain variable region comprising the amino acid sequence preferably having at least 70%, preferably at least 80%, or more preferably at least 90%, identity to SEQ ID NO: 8.

Preferably, the heavy chain comprises the amino acid sequence having at least 70%, preferably at least 80%, or more preferably at least 90%, identity to SEQ ID NO: 9.

Preferably, the light chain comprises the amino acid sequence having at least 70%, preferably at least 80%, or more preferably at least 90%, identity to SEQ ID NO: 10.

Preferably, the antibody or antigen-binding fragment is conjugated with agents such as therapeutic compounds, fluorescent markers, chemiluminescent markers, colorimetric indicators, enzymatic labels, radioactive isotopes, and affinity tags.

For an additional aspect of the present disclosure, there is provision for a polynucleotide encoding the antibody or antigen-binding fragment thereof of any one of above-mentioned.

For another purpose of the present disclosure, further provides a reagent for predicting or diagnosing a sADAM9v2-related disease, determining drug efficacy after treatment with a sADAM9v2 inhibitor, or screening for a subject in whom treatment with a sADAM9v2 inhibitor is highly effective, wherein the reagent comprises the antibody or antigen-binding fragment thereof of above-mentioned.

For another purpose of the present disclosure, further provides a method for predicting or diagnosing a sADAM9v2-related disease or a predisposition for developing the sADAM9v2-related disease in a subject, wherein the method comprises the steps of: (a) contacting a sample isolated from the subject with the antibody or antigen-binding fragment thereof of any one of above-mentioned; (b) detecting a sADAM9v2 protein in the sample by detecting binding between the antibody or antigen-binding fragment thereof and the sample; and (c) comparing the level of the sADAM9v2 protein in the sample to a control, wherein a higher sADAM9v2 protein level than the control indicates that the subject suffers from the disease or has a risk of developing the disease.

Preferably, the sADAM9v2-related disease may be a cancer expressing sADAM9v2; optionally, the sADAM9v2-related disease is a cancer overexpressing sADAM9v2.

Preferably, the cancer may be a prostate cancer.

For another purpose of the present disclosure, further provides a use of the antibody or antigen-binding fragment thereof of any one of above-mentioned for manufacturing a pharmaceutical composition for treating sADAM9v2-related disease.

For another purpose of the present disclosure, further provides a pharmaceutical composition, comprising an effective dose of an antibody or antigen-binding fragment thereof of any one of above-mentioned as an active ingredient and a pharmaceutically acceptable carrier.

As disclosed above, the present disclosure provides a monoclonal antibody developed using the specificity of soluble ADAM9 variants secreted in the periphery of prostate cancer, which can detect the occurrence of prostate cancer at an early stage.

BRIEF DESCRIPTION OF DRAWINGS

The following drawings form part of the present specification and are included to further demonstrate certain aspects of the present disclosure, which can be better understood by reference to the drawing in combination with the detailed description of specific embodiments presented herein.

DETAILED DESCRIPTION OF INVENTION

Figure 1:
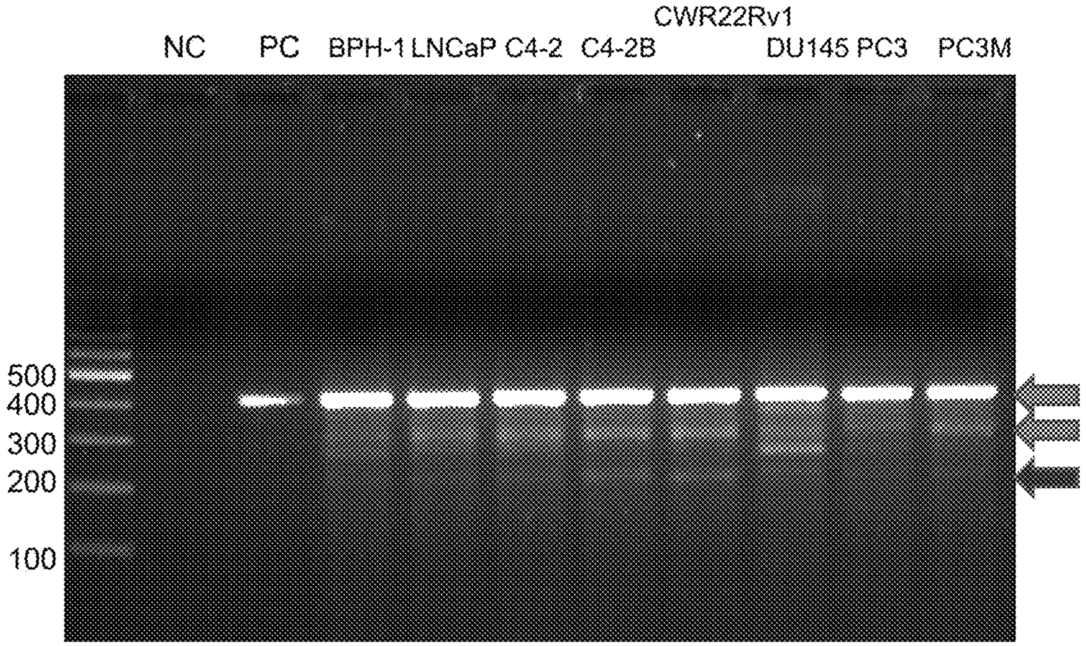
FIG. 1 presents the outcomes of PCR analysis, revealing a discrepancy between the length of ADAM9 and a predetermined length. The cell lines engaged in these investigations encompass NC (representing negative control, without ADAM9), PC (indicative of positive control of ADAM9 gene), BPH-1 (a cell line representing Benign Prostate Hyperplasia-1), LNCaP (designated as a cancer cell line derived from a prostate cancer patient exhibiting lymph node metastasis), C4-2 (an offshoot of the LNCaP linage characterized by androgen insensitive), C4-2B (a subset of C4-2 cells extracted from bone metastasis in mice model), CWR22Rv1 (a prostate cancer cell line exhibiting an androgen receptor mutation, ARV7 mutation), DU145 (a prostate cancer cell line sourced from brain metastasis of prostate cancer patients), PC3 (prostate cancer cell line obtained from patient with prostate cancer bone metastasis), and PC3M (a variation of the PC3 cell demonstrating pronounced bone metastasis in animal model).

For the descriptions herein and the appended claims, the singular forms "a", and "an" include plural referents unless the context clearly indicates otherwise. Thus, for example, reference to "a protein" includes more than one protein, and reference to "a compound" refers to more than one compound. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention. For example, "1 to 50," includes "2 to 25," "5 to 20," "25 to 50," "1 to 10," etc.

All publications, patents, patent applications, and other documents referenced in this disclosure are hereby incorporated by reference in their entireties for all purposes to the same extent as if each individual publication, patent, patent application or other document were individually indicated to be incorporated by reference herein for all purposes.

It is to be understood that both the foregoing general description, including the drawings, and the following detailed description are exemplary and explanatory only and are not restrictive of this disclosure.

The technical and scientific terms used in the descriptions herein will have the meanings commonly understood by one of ordinary skill in the art, unless specifically defined otherwise.

I. sADAM9v2 Antibody or Antigen-Binding Fragment Thereof

An antibody or antigen-binding fragment thereof is provided, which binds to a sADAM9v2 protein or a partial peptide thereof, wherein the antibody or antigen-binding fragment thereof comprises:

- a heavy chain comprising
  - CDR1 comprising an amino acid sequence of SEQ ID NO: 1,
  - CDR2 comprising an amino acid sequence of SEQ ID NO: 2, and
  - CDR3 comprising an amino acid sequence of SEQ ID NO: 3; and
- a light chain comprising
  - CDR1 comprising an amino acid sequence of SEQ ID NO: 4,
  - CDR2 comprising an amino acid sequence of SEQ ID NO: 5, and
  - CDR3 comprising an amino acid sequence of SEQ ID NO: 6.

In one embodiment, the antibody or antigen-binding fragment thereof comprising a heavy chain variable region comprising the amino acid sequence having at least 70%, preferably at least 80%, or more preferably at least 90%, identity to SEQ ID NO: 7 and a light chain variable region comprising the amino acid sequence preferably having at least 70%, preferably at least 80%, or more preferably at least 90%, identity to SEQ ID NO: 8.

In one embodiment, the heavy chain comprising the amino acid sequence having at least 70%, preferably at least 80%, or more preferably at least 90%, identity to SEQ ID NO: 9.

In one embodiment, the light chain comprising the amino acid sequence having at least 70%, preferably at least 80%, or more preferably at least 90%, identity to SEQ ID NO: 10.

An antibody (interchangeably used in plural form) is an immunoglobulin molecule capable of specific binding to a target antigen (e.g., sADAM9v2 in the present disclosure), through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', $F(ab')_2$, Fv), single chain (scFv), mutants thereof, fusion proteins comprising an antibody portion, humanized antibodies, chimeric antibodies, diabodies, nanobodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. The term "isolated antibody" used herein refers to an antibody substantially free from naturally associated molecules, i.e., the naturally associated molecules constituting at most 20% by dry weight of a preparation containing the antibody. Purity can be measured by any appropriate method, e.g., column chromatography, polyacrylamide gel electrophoresis, and HPLC.

A typical antibody molecule comprises a heavy chain variable region ($V_H$) and a light chain variable region ($V_L$), which are usually involved in antigen binding. The $V_H$ and $V_L$ regions can be further subdivided into regions of hypervariability, also known as "complementarity determining regions" ("CDR"), interspersed with regions that are more conserved, which are known as "framework regions" ("FR"). Each VH and VL is typically composed of three CDRs and four FRs, arranged from amino-terminus to carboxy-terminus in the following order: FR1, CDR1, FR2, CDR2, FR3, CDR3, and FR4. The extent of the framework region and CDRs can be precisely identified using methodology known in the art, for example, by the Kabat definition, the IMGT definition, the Chothia definition, the AbM definition, and/or the contact definition, all of which are well known in the art. See, e.g., Kabat, E. A., et al. (1991) Sequences of Proteins of Immunological Interest, Fifth Edition, U.S. Department of Health and Human Services, NIH Publication No. 91-3242; IMGT®, the international ImMunoGeneTics Information System® http://www.imgt.org, Lefranc, M.-P. et al., Nucleic Acids Res., 27:209-212 (1999); Ruiz, M. et al., Nucleic Acids Res., 28:219-221 (2000); Lefranc, M.-P., Nucleic Acids Res., 29:207-209 (2001); Lefranc, M.-P., Nucleic Acids Res., 31:307-310 (2003); Lefranc, M.-P. et al., In Silico Biol., 5, 0006 (2004) [Epub], 5:45-60 (2005); Lefranc, M.-P. et al., Nucleic Acids Res., 33:D593-597 (2005); Lefranc, M.-P. et al., Nucleic Acids Res., 37:D1006-1012 (2009); Lefranc, M.-P. et al., Nucleic Acids Res., 43:D413-422 (2015); Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004). As used herein, a CDR may refer to the CDR defined by any method known in the art. Two antibodies having the same CDR means that the two antibodies have the same amino acid sequence of that CDR as determined by the same method, for example, the IMGT definition.

In some embodiments, the isolated anti-sADAM9v2 antibody as described herein can bind and inhibit the activity of the sADAM9v2 by at least 50% (e.g., 60%, 70%, 80%, 90%, 95% or greater). The apparent inhibition constant (Kiapp or Ki, app), which provides a measure of inhibitor potency, is related to the concentration of inhibitor required to reduce enzyme activity and is not dependent on enzyme concentrations. The inhibitory activity of an anti-sADAM9v2 antibody described herein can be determined by routine methods known in the art.

Any of the antibodies described herein can be either monoclonal or polyclonal. A "monoclonal antibody" refers to a homogenous antibody population and a "polyclonal antibody" refers to a heterogeneous antibody population. These two terms do not limit the source of an antibody or the manner in which it is made.

In some embodiments, the anti-sADAM9v2 antibody described herein binds the same epitope with sADAM9v2 antigen as a reference antibody disclosed herein or competes against the reference antibody from binding to the sADAM9v2 antigen. An "epitope" refers to the site on a target compound that is bound by an antibody such as a Fab or full-length antibody. An epitope can be linear, which is typically 6-15 amino acid in length. Alternatively, the epitope can be conformational. An antibody that binds the same epitope as a reference antibody described herein may bind to exactly the same epitope or a substantially overlapping epitope (e.g., containing less than 3 non-overlapping amino acid residue, less than 2 non-overlapping amino acid residues, or only 1 non-overlapping amino acid residue) as the reference antibody. Whether two antibodies compete against each other from binding to the cognate antigen can be determined by a competition assay, which is well known in the art. Such antibodies can be identified as known to those skilled in the art, e.g., those having substantially similar structural features (e.g., complementary determining regions), and/or those identified by assays known in the art. For example, competition assays can be performed using one of the reference antibodies to determine whether a candidate antibody binds to the same epitope as the reference antibody or competes against its binding to the sADAM9v2 antigen.

In one example, the antibody used in the methods described herein can be a humanized antibody. Humanized antibodies refer to forms of non-human (e.g. murine) antibodies that are specific chimeric immunoglobulins, immunoglobulin chains, or antigen-binding fragments thereof that contain minimal sequence derived from non-human immunoglobulin. For the most part, humanized antibodies are human inmunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, or six) which are altered with respect to the original antibody, which are also termed one or more CDRs "derived from" one or more CDRs from the original antibody. Humanized antibodies may also involve affinity maturation.

In some embodiments, the anti-sADAM9v2 antibodies described herein specifically bind to the corresponding target antigen or an epitope thereof. An antibody that "specifically binds" to an antigen or an epitope is a term well understood in the art. A molecule is said to exhibit "specific binding" if it reacts more frequently, more rapidly, with greater duration and/or with greater affinity with a particular target antigen than it does with alternative targets. An antibody "specifically binds" to a target antigen or epitope if it binds with greater affinity, avidity, more readily, and/or with greater duration than it binds to other substances. For example, an antibody that specifically (or preferentially) binds to an antigen (e.g., human s ADAM9v2) or an antigenic epitope therein is an antibody that binds this target antigen with greater affinity, avidity, more readily, and/or with greater duration than it binds to other antigens or other epitopes in the same antigen. It is also understood with this definition that, for example, an antibody that specifically binds to a first target antigen may or may not specifically or preferentially bind to a second target antigen. As such, "specific binding" or "preferential binding" does not necessarily require (although it can include) exclusive binding. In some examples, an antibody that "specifically binds" to a target antigen or an epitope thereof may not bind to other antigens or other epitopes in the same antigen (e.g., binding not detectable in a conventional assay).

In some embodiments, the antibodies described herein specifically binds to sADAM9v2 of a specific species (e.g., human sADAM9v2) as relative to sADAM9v2 from other species. For example, the antibodies described herein may specifically binds to human sADAM9v2 as relative to mouse sADAM9v2. In other embodiments, the antibodies described herein may cross-react with human sADAM9v2 and one or more sADAM9v2 from a non-human species (e.g., a non-human primate such as macaque). In some embodiments, the antibodies cross-react with human and rhesus macaque with similar binding affinity but have significantly lower binding affinity to mouse sADAM9v2. In some embodiments, an anti-sADAM9v2 antibody as described herein has a suitable binding affinity for the target antigen (e.g., human sADAM9v2) or antigenic epitopes thereof.

As used herein, "binding affinity" refers to the apparent association constant or KA, which is the ratio of association and dissociation constants, K-on and K-off, respectively. The $K_A$ is the reciprocal of the dissociation constant ($K_D$). The anti-sADAM9v2 antibody described herein may have a binding affinity ($K_D$) of at least $10^{-8}$, $10^{-9}$, $10^{-10}$ M, $10^{-11}$M or lower for the target antigen or antigenic epitope. For example, the anti-sADAM9v2 antibody may have a binding affinity of $10^{-9}$ M, $10^{-10}$ M or lower to sADAM9v2. An increased binding affinity corresponds to a decreased value of $K_D$. Higher affinity binding of an antibody for a first antigen relative to a second antigen can be indicated by a higher $K_A$ (or a smaller numerical value $K_D$) for binding the first antigen than the $K_A$ (or numerical value $K_D$) for binding the second antigen. In such cases, the antibody has specificity for the first antigen (e.g., a first protein in a first conformation or mimic thereof) relative to the second antigen (e.g., the same first protein in a second conformation or mimic thereof; or a second protein). In some embodiments, the anti-sADAM9v2 antibodies described herein have a higher binding affinity (a higher $K_A$ or smaller KL) to sADAM9v2 as compared to the binding affinity to another cytokines or chemokines. In some embodiments, the anti-sADAM9v2 antibody may have a higher binding affinity to a sADAM9v2 of a specific species (e.g., human sADAM9v2) than that to a sADAM9v2 from a different species (e.g., mouse). Differences in binding affinity (e.g., for specificity or other comparisons) can be at least 1.5, 2, 2.5, 3, 4, 5, 10, 15, 20, 37.5, 50, 70, 80, 91, 100, 500, 1,000, 5,000, 10,000 or $10^5$ folds. In some embodiments, any of the anti-sADAM9v2 antibodies may be further affinity matured to increase the binding affinity of the antibody to the target antigen or antigenic epitope thereof.

Binding affinity (or binding specificity) can be determined by a variety of methods including equilibrium dialysis, equilibrium binding, gel filtration, ELISA, surface plasmon resonance (SPR), florescent activated cell sorting (FACS) or spectroscopy (e.g., using a fluorescence assay). Exemplary conditions for evaluating binding affinity are in HBS-P buffer (10 mM HEPES pH7.4, 150 mM NaCl, 0.005% (v/v) surfactant P20) and PBS buffer (10 mM $PO_4^{-3}$, 137 mM NaCl, and 2.7 mM KCl). These techniques can be used to measure the concentration of bound proteins as a function of target protein concentration. The concentration of bound protein ([Bound]) is generally related to the concentration of free target protein ([Free]) by the following equation:

$$[\text{Bound}] = [\text{Free}]/(Kd + [\text{Free}])$$

It is not always necessary to make an exact determination of KA, though, since sometimes it is sufficient to obtain a quantitative measurement of affinity, e.g., determined using a method such as ELISA or FACS analysis, is proportional to KA, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

In some instances, the amino acid residue variations can be conservative amino acid residue substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al, eds., Second Edition, Cold Spring Harbor Laboratory Press, Cold Spring Harbor, New York, 1989, or Current Protocols in Molecular Biology, F.M. Ausubel, et al., eds., John Wiley & Sons, Inc., New York.

In some embodiments, the heavy chain of any of the anti-sADAM9v2 antibodies as described herein may further comprise a heavy chain constant region (5 CH) or a portion thereof (e.g., CH1, CH2, CH3, or a combination thereof). The heavy chain constant region can of any suitable origin, e.g., human, mouse, rat, or rabbit. In one specific example, the heavy chain constant region is from a human IgG (a gamma heavy chain), e.g., IgG1, IgG2, or IgG4. In one example, the heavy chain constant region is of subclass IgG1.

The light chain of any of the anti-sADAM9v2 antibodies described herein may further comprise a light chain constant region (CL), which can be any CL known in the art. In some examples, the CL is a kappa light chain. In other examples, the CL is a lambda light chain. Antibody heavy and light chain constant regions are well known in the art, e.g., those provided in the IMGT database (www.imgt.org) or at www.vbase2.org/vbstat.php., both of which are incorporated by reference herein.

As described herein, the anti-sADAM9v2 antibody can be in any antibody form, including, but not limited to, intact (i.e., full-length) antibodies, antigen-binding fragments thereof (such as Fab, Fab', F(ab')2, Fv), single chain antibodies, bi-specific antibodies, or nanobodies.

II. Preparation of Anti-sADAM9v2 Antibodies

Antibodies capable of binding sADAM9v2 as described herein can be made by any method known in the art. See, for example, Harlow and Lane, (1998) Antibodies: A Laboratory Manual, Cold Spring Harbor Laboratory, New York.

In some embodiments, antibodies specific to a target antigen (e.g., sADAM9v2) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the activity of sADAM9v2. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are XenomouseR™ from Amgen, Inc. (Fremont, CA) and HuMAb-MouseR™ and TC Mouse™ from Medarex, Inc. (Princeton, NJ) or H2L2 mice from Harbour Antibodies BV (Holland). In another alternative, antibodies may be made recombinantly by phage display or yeast technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, $F(ab')_2$ fragments can be produced by pepsin digestion of an antibody molecule, and Fab fragments that can be generated by reducing the disulfide bridges of $F(ab')_2$ fragments. Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as *E. coli* cells, simian COS cells, Chinese hamster ovary (CHO) cells, human HEK293 cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In one example, epitope mapping can be accomplished use H/D-Ex (hydrogen deuterium exchange) coupled with proteolysis and mass spectrometry. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identity residues required, sufficient, and/or necessary for epitope binding. For example, domain swapping experiments can be performed using a mutant of a target antigen in which various fragments of the sADAM9v2 polypeptide have been replaced (swapped) with sequences from a closely related, but antigenically distinct protein (such as CD-28 protein). By assessing binding of the antibody to the mutant sADAM9v2, the importance of the particular antigen fragment to antibody binding can be assessed. Alternatively, competition assays can be performed using other antibodies known to bind to the same antigen to determine whether an antibody binds to the same epitope as the other antibodies. Competition assays are well known to those of skill in the art.

In some examples, an anti-sADAM9v2 antibody is prepared by recombinant technology as exemplified below. Nucleic acids encoding the heavy and light chain of an anti-sADAM9v2 antibody as described herein can be cloned into one expression vector, each nucleotide sequence being in operable linkage to a suitable promoter. In one example, each of the nucleotide sequences encoding the heavy chain and light chain is in operable linkage to a distinct promoter. Alternatively, the nucleotide sequences encoding the heavy chain and the light chain can be in operable linkage with a single promoter, such that both heavy and light chains are expressed from the same promoter. When necessary, an internal ribosomal entry site (IRES) can be inserted between the heavy chain and light chain encoding sequences.

In some examples, the nucleotide sequences encoding the two chains of the antibody are cloned into two vectors, which can be introduced into the same or different cells. When the two chains are expressed in different cells, each of them can be isolated from the host cells expressing such and the isolated heavy chains and light chains can be mixed and incubated under suitable conditions allowing for the formation of the antibody.

Generally, a nucleic acid sequence encoding one or all chains of an antibody can be cloned into a suitable expression vector in operable linkage with a suitable promoter using methods known in the art. For example, the nucleotide sequence and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. The selection of expression vectors/promoter would depend on the type of host cells for use in producing the antibodies.

Regulatable promoters can be used. Such regulatable promoters include those using the lac repressor from *E. coli* as a transcription modulator to regulate transcription from lac operator bearing mammalian cell promoters [Brown, M. et al., Cell, 49:603-612 (1987)], those using the tetracycline repressor (tetR) [Gossen, M., and Bujard, H., Proc. Natl. Acad. Sci. USA 89:5547-555115 (1992); Yao, F. et al., Human Gene Therapy, 9:1939-1950 (1998); Shockelt, R. et al., Proc. Natl. Acad. Sci. USA, 92:6522-6526 (1995)]. Other systems include FK506 dimer, VP16 or p65 using astradiol, RU486, diphenol murislerone, or rapamycin. Inducible systems are available from Invitrogen, Clontech and Ariad, among others.

Regulatable promoters that include a repressor with the operon can be used. In one embodiment, the lac repressor from *E. coli* can function as a transcriptional modulator to regulate transcription from lac operator-bearing mammalian cell promoters [M. Brown et al., Cell, 49:603-612 (1987)]; Gossen and Bujard (1992); [M. Gossen et al., Natl. Acad. Sci. USA, 89:5547-5551(1992)] combined the tetracycline repressor (tetR) with the transcription activator (VP 16) to create a tetR-mammalian cell transcription activator fusion protein, tTa (tetR-VP 16), with the tetO bearing minimal promoter derived from the human cytomegalovirus (hCMV) promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., Human Gene Therapy). One particular advantage of this tetracycline inducible switch is that it does not require the use of a tetracycline repressor-mammalian cells transactivator or repressor fusion protein, which in some instances can be toxic to cells (Gossen 5 et al, Natl. Acad. Sci. USA, 89:5547-5551 (1992); Shockett et al., Proc. Natl. Acad. Sci. USA, 92:6522-6526 (1995)), to achieve its regulatable effects.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art. Examples of polyadenylation signals useful to practice the methods described herein include, but are not limited to, human collagen I polyadenylation signal, human collagen II polyadenylation signal, and SV40 polyadenylation signal.

One or more vectors (e.g., expression vectors) comprising nucleic acids encoding any of the antibodies may be introduced into suitable host cells for producing the antibodies. The host cells can be cultured under suitable conditions for expression of the antibody or any polypeptide chain thereof. Such antibodies or polypeptide chains thereof can be recovered by the cultured cells (e.g., from the cells or the culture supernatant) via a conventional method, e.g., affinity purification. If necessary, polypeptide chains of the antibody can be incubated under suitable conditions for a suitable period of time allowing for production of the antibody.

In some embodiments, methods for preparing an antibody described herein involve a recombinant expression vector that encodes both the heavy chain and the light chain of an anti-sADAM9v2 antibody, as also described herein. The recombinant expression vector can be introduced into a suitable host cell (e.g., a dhfr- CHO cell) by a conventional method, e.g., calcium phosphate mediated transfection. Positive transformant host cells can be selected and cultured under suitable conditions allowing for the expression of the two polypeptide chains that form the antibody, which can be recovered from the cells or from the culture medium. When necessary the two chains recovered from the host cells can be incubated under suitable conditions allowing for the formation of the antibody.

In one example, two recombinant expression vectors are provided, one encoding the heavy chain of the anti-sADAM9v2 antibody and the other encoding the light chain of the anti-sADAM9v2 antibody. Both of the two recombinant expression vectors can be introduced into a suitable host cell (e.g., dhfr- CHO cell) by a conventional method, e.g., calcium phosphate-mediated transfection.

Alternatively, each of the expression vectors can be introduced into a suitable host cells. Positive transformants can be selected and cultured under suitable conditions allowing for the expression of the polypeptide chains of the antibody. When the two expression vectors are introduced into the same host cells, the antibody produced therein can be recovered from the host cells or from the culture medium. If necessary, the polypeptide chains can be recovered from the host cells or from the culture medium and then incubated under suitable conditions allowing for formation of the antibody. When the two expression vectors are introduced into different host cells, each of them can be recovered from the corresponding host cells or from the corresponding culture media. The two polypeptide chains can then be incubated under suitable conditions for formation of the antibody.

Standard molecular biology techniques are used to prepare the recombinant expression vector, transfect the host cells, select for transformants, culture the host cells and recovery of the antibodies from the culture medium. For example, some antibodies can be isolated by affinity chromatography with a Protein A, Protein G or Protein L coupled matrix.

Any of the nucleic acids encoding the heavy chain, the light chain, or both of an anti-sADAM9v2 antibody as described herein, vectors (e.g., expression vectors) containing such; and host cells comprising the vectors are within the scope of the present disclosure.

III. Pharmaceutical Compositions

The antibodies, as well as the encoding nucleic acids or nucleic acid sets, vectors comprising such, or host cells comprising the vectors, as described herein can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The anti-sADAM9v2 antibody containing pharmaceutical composition disclosed herein may further comprise a suitable buffer agent. A buffer agent is a weak acid or base used to maintain the pH of a solution near a chosen value after the addition of another acid or base. In some examples, the buffer agent disclosed herein can be a buffer agent capable of maintaining physiological pH despite changes in carbon dioxide concentration (produced by cellular respiration). Exemplary buffer agents include, but are not limited to a HEPES (4-(2-hydroxyethyl)-1-piperazineethanesulfonic acid) buffer, Dulbecco's phosphate-buffered saline (DPBS) buffer, or Phosphate-buffered Saline (PBS) buffer. Such buffers may comprise disodium hydrogen phosphate and sodium chloride, or potassium dihydrogen phosphate and potassium chloride.

In some embodiments, the buffer agent in the pharmaceutical composition described herein may maintain a pH value of about 5-8. For example, the pH of the pharmaceutical composition can be about 7.1, 7.2, 7.3, 7.4, 7.5, 7.6, 7.7, 7.8, 7.9, or 8.0. In other examples, the pharmaceutical composition may have a pH value lower than 7, for example, about 7, 6.8, 6.5, 63, 6, 5.8, 5.5, 5.3, or 5.

The pharmaceutical composition described herein comprises one or more suitable salts. A salt is an ionic compound that can be formed by the neutralization reaction of an acid and a base. (Skoog, D. A; West, D. M.; Holler, J. F.; Crouch, S. R. (2004). "chapters 14 to 16". Fundamentals of Analytical Chemistry (8th ed.)). Salts are composed of related numbers of cations (positively charged ions) and anions (negative ions) so that the product is electrically neutral (without a net charge). An ion, as described herein, are atoms or molecules which have gained or lost one or more valence electrons giving the ion a net positive or negative charge. If the chemical species has more protons than electrons, it carries a net positive charge. If there are more electrons than protons, the species has a negative charge.

A cation (+), as described herein, is an ion with fewer electrons than protons, giving it a positive charge. (Douglas W. Haywick, (2007-2008). "Elemental Chemistry"). A cation with one positive charge can be called a monovalent cation; a cation with more than one positive charge can be called a polyvalent or multivalent cation. Non limiting examples of monovalent cations are hydrogen ($H^+$), sodium ($Na^+$), potassium ($K^+$), ammonium ($NH^{4+}$), Lithium ($Li^+$), cuprous ($Cu^+$), silver ($Ag^+$), etc. Non limiting examples of multivalent cations are magnesium ($Mg^{2+}$), calcium ($Ca^{2+}$), barium ($Ba^{2+}$), beryllium ($Be^{2+}$), cupric ($Cu^{2+}$), ferrous ($Fe^{2+}$), ferric ($Fe^{3+}$), lead(II) ($Pb^{2+}$), lead(IV) ($Pb^{4+}$), manganese(II) ($Mn^{2+}$) strontium ($Sr^{2+}$), tin(IV) ($Sn^{4+}$), zinc ($Zn^{2+}$), etc.

An anion, as described herein, is an ion with more electrons than protons, giving it a net negative charge. Non limiting examples of anions are azide ($N^{3-}$), bromide ($Br^-$), chloride ($Cl^-$), fluoride ($F^-$), hydride ($H^-$), iodide ($I^-$), nitride ($N^-$), Oxide ($O^{2-}$), sulfide ($S^{2-}$), carbonate ($CO_3^{2-}$), hydrogen carbonate ($HCO_3^-$), hydrogen sulfate ($HSO_4^-$), hydroxide ($OH^-$), dihydrogen phosphate ($H_2PO_4^-$), sulfate ($SO_4^{2-}$), sulfite ($SO_3^{2-}$), silicate ($SiO_3^{2-}$), etc.

Suitable salts for use in the pharmaceutical compositions described herein may contain a monovalent cation and a monovalent or multi-valent anion. Alternatively, the salts for use in the pharmaceutical compositions described herein may contain a monovalent or multi-valent cation and a monovalent anion. Exemplary salts include, but are not limited to, potassium chloride (KCl), sodium chloride (NaCl), calcium chloride ($CaCl_2$)), Magnesium chloride ($MgCl_2$), Magnesium Sulfate($MgSO_4$), Sodium Bicarbonate ($NaHCO_3$), Ammonium sulfate($(NH_4)_2SO_4$), calcium carbonate ($Ca_2CO_3$), or a combination thereof.

The pharmaceutical composition described herein comprises one or more suitable surface-active agents, such as a surfactant. Surfactants are compounds that lower the surface tension (or interfacial tension) between two liquids, between a gas and a liquid, or between a liquid and a solid. Surfactants may act as detergents, wetting agents, emulsifiers, foaming agents, and dispersants. Suitable surfactants include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

A pharmaceutical composition, comprising an anti-sADAM9v2 described herein, may comprise one or more amino acids. Exemplary amino acids include, but are not limited to, glycine, histidine, or arginine.

The pharmaceutical composition may also comprise one or more antioxidants. An antioxidant, as used herein, is an agent that prevents or delays oxidative degradation of the active ingredients contained in the composition. The antioxidants used herein may be phenolic antioxidants (sometimes called true antioxidants), reducing agents, or chelating agents. Phenolic antioxidants are sterically hindered phenols that react with free radicals, blocking the chain reaction. Reducing agents are compounds that have lower redox potentials and, thus, are more readily oxidized than the drug they are intended to protect. Reducing agents scavenge oxygen from the medium and, thus, delay or prevent drug oxidation. Chelating agents are sometimes called antioxidant synergists. Metal ions, such as $Co^{2+}$, $Cu^{2+}$, $Fe^{3+}$, $Fe^{2+}$, and $Mn^{2+}$, shorten the induction period and increase the oxidation rate. Trace amounts of these metal ions are frequently introduced to drug products during manufacturing. Chelating agents do not possess antioxidant activity as such, but enhance the action of phenolic antioxidants by reacting with catalyzing metal ions to make them inactive.

The pharmaceutical composition described herein may also comprise a sugar derivative. A sugar derivative, as used herein, encompasses sugars and organic compounds derived from sugar. In some examples, the sugar derivative can be a non-reducing sugar, a sugar alcohol, a polyol, a disaccharide or a polysaccharide.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol: alkyl parabens such as methyl or propyl paraben; catechol; resorcinol; cyclohexanol; 3-pentanol; and meresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In some examples, the pharmaceutical composition described herein comprises liposomes containing the antibodies (or the encoding nucleic acids) which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The antibodies, or the encoding nucleic acid(s), may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vnylalcohol)), polylactides (U.S. Pat. No. 3,773,919), copolymers of L-glutamic acid and 7 ethyl-L20 glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

In other examples, the pharmaceutical composition described herein can be formulated in a sustained release format, which affects binding selectively to tissue or tumors by implementing certain protease biology technology, for example, by peptide masking of the antibody's antigen binding site to allow selective protease cleavability by one or multiple proteases in the tumor microenvironment, such as Probody™ or Conditionally Active Biologics-M. An activation may be formulated to be reversible in a normal microenvironment.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an 10 oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 .im, particularly 0.1 and 0.5 .im, and have a pH in the range of 5.5 to 8.0. The emulsion compositions can be those prepared by mixing an antibody with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

IV. Therapeutic Applications

Any of the antibodies, as well as the encoding nucleic acids or nucleic acid sets, vectors comprising such, or host cells comprising the vectors, described herein are useful for treating sADAM9v2 mediated disorders. sADAM9v2 mediated diseases, as used herein, refer to any medical condition associated with increased levels of sADAM9v2 or increased sensitivity to sADAM9v2. Non-limiting examples of sADAM9v2 mediated diseases are prostate cancer, etc.

To practice the method disclosed herein, an effective amount of the pharmaceutical composition described herein can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the antibodies as described herein can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having inflammatory diseases, autoimmune diseases, cancer, infectious diseases or other disorders requiring modulation of the immune response. A subject having a target disease or disorder can be identified by routine medical examination, e.g., laboratory tests, organ functional tests, CT scans, or ultrasounds. A subject suspected of having any of such target disease/disorder might show one or more symptoms of the disease/disorder. A subject at risk for the disease/disorder can be a subject having one or more of the risk factors for that disease/disorder.

As used herein, "an effective amount" refers to the amount of each active agent required to confer therapeutic effect on the subject, either alone or in combination with one or more other active agents. In some embodiments, the therapeutic effect is reduced sADAM9v2 activity.

"Overexpress", as used herein, refers to cancer cells have surface expression of sADAM9v2 significantly higher than that of normal cells.

Determination of whether an amount of the antibody achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation.

It is generally preferred that a maximum dose of the individual components or combinations thereof be used, that is, the highest safe dose according to sound medical judgment.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a target disease/disorder. Alternatively, sustained continuous release formulations of an antibody may be appropriate. Various formulations and devices for achieving sustained release are known in the art.

In one example, dosages for an antibody as described herein may be determined empirically in individuals who have been given one or more administration(s) of the antibody. Individuals are given incremental dosages of the antagonist. To assess efficacy of the antagonist, an indicator of the disease/disorder can be followed.

Generally, for administration of any of the antibodies described herein, an initial candidate dosage can be about 2 mg/kg. For the purpose of the present disclosure, a typical daily, weekly, every two weeks, or every three weeks dosage might range from about any of 0.1 μg/kg to 3 μg/kg to 30 μg/kg to 100 μg/kg to 300 μg/kg to 0.6 mg/kg, 1 mg/kg, 3 mg/kg, to 10 mg/kg, to 30 mg/kg to 100 mg/kg or more, depending on the factors mentioned above. For repeated administrations over several days, weeks, months, or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering an initial dose of about 3 mg/kg every 3 weeks, followed by a maintenance dose of about 1 mg/kg of the antibody once in 6 weeks, or followed by a maintenance dose of about 1 mg/kg every 3 weeks. However, other dosage regimens may be useful, depending on the pattern of pharmacokinetic decay that the practitioner wishes to achieve. For example, dosing of 1 mg/kg once in every 3 weeks in combination treatment with at least one additional immune therapy agent is contemplated. In some embodiments, dosing ranging from about 3 μg/mg to about 3 mg/kg (such as about 3 μg/mg, about 10 μg/mg, about 30 μg/mg, about 100 μg/mg, about 300 μg/mg, about 1 mg/kg, and about 3 mg/kg) may be used. In some embodiments, dosing frequency is once every week, every 2 weeks, every 3 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

In some embodiments, for an adult patient of normal weight, doses ranging from about 0.1 to 5.0 mg/kg may be administered. In some examples, the dosage of the anti-sADAM9v2 antibody described herein can be 10 mg/kg. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of an antibody as described herein will depend on the specific antibody, antibodies, and/or non-antibody peptide (or compositions thereof) employed, the type and severity of the disease/disorder, whether the antibody is administered for preventive or therapeutic purposes, previous therapy, the patient's clinical history and response to the antagonist, and the discretion of the attending physician. Typically, the clinician will administer an antibody, until a dosage is reached that achieves the desired result. In some embodiments, the desired result is a reduction of the size of the tumor, increased progression free survival period and/or overall survival. Methods of determining whether a dosage resulted in the desired result would be evident to one of skill in the art. Administration of one or more antibodies can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced dose, e.g., either before, during, or after developing a target disease or disorder As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder. Alleviating a target disease/disorder includes delaying the development or progression of the disease or reducing disease severity.

Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

In some embodiments, the antibodies described herein are administered to a subject in need of the treatment at an amount sufficient to inhibit the activity of the target antigen by at least 20% (e.g., 30%, 40%, 50%, 60%, 70%, 80%, 90% or greater) in vivo. In other embodiments, the antibody is administered in an amount effective in reducing the activity level of a target antigen by at least 20% (e.g., 30%, 40%, 50%, 60%, 70%, 80%, 90% or greater).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered parenterally, topically, orally, by inhalation spray, rectally, nasally, buccally, vaginally or via an implanted reservoir. The term "parenteral" as used herein includes subcutaneous, intracutaneous, intravenous, intraperitoneal, intratumor, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipient is infused. Physiologically acceptable excipients may include, for example, 5% dextrose, 0.9% saline. Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an antibody is administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods and Applications of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338.

Therapeutic compositions containing a polynucleotide (e.g., those encoding the antibodies described herein) are administered in a range of about 100 ng to about 200 mg of DNA for local administration in a gene therapy protocol. In some embodiments, concentration ranges of about 500 ng to about 50 mg, about 1 μg to about 2 mg, about 5 μg to about 500 μg, and about 20 μg to about 100 μg of DNA or more can also be used during a gene therapy protocol.

The therapeutic polynucleotides and polypeptides described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373: ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel. Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

The particular dosage regimen, i.e., dose, timing and repetition, used in the method described herein will depend on the particular subject and that subject's medical history. In some embodiments, more than one antibody, or a combination of an antibody and another suitable therapeutic agent, may be administered to a subject in need of the treatment. The antibody can also be used in conjunction with other agents that serve to enhance and/or complement the effectiveness of the agents. Treatment efficacy for a target disease/disorder can be assessed by methods well-known in the art.

The anti-sADAM9v2 antibody and treatment methods involving such as described in the present disclosure may be utilized in combination with other types of therapy for the target disease or disorder disclosed herein. The term "in combination" in this context means that the antibody composition and the therapeutic agent are given either simultaneously or sequentially. Examples include chemotherapy, immune therapy (e.g. therapies involving anti-inflammatory drugs, immunosuppressant, therapeutic antibodies, antibodies, CAR T cells, or cancer vaccines), surgery, radiation, gene therapy, and so forth, or anti-infection therapy. Such therapies can be administered simultaneously or sequentially (in any order) with the treatment according to the present disclosure.

When the antibody composition described here is co-used with a second therapeutic agent, a sub-therapeutic dosage of either the composition or of the second agent, or a sub-therapeutic dosage of both, can be used in the treatment of a subject having, or at risk of developing a disease or disorder associated with the cell signaling mediated by sADAM9v2. A "sub-therapeutic dose" as used herein refers to a dosage, which is less than that dosage which would produce a therapeutic result in the subject if administered in the absence of the other agent or agents. Thus, the sub-therapeutic dose of an agent is one which would not produce the desired therapeutic result in the subject in the absence of the administration of the anti-sADAM9v2 antibody described herein. Therapeutic doses of many agents that are in clinical use are well known in the field of medicine, and additional therapeutic doses can be determined by those of skill without undue experimentation. Therapeutic dosages have been extensively described in references such as Remington's Pharmaceutical Sciences, 18th ed., 1990; as well as many other medical references relied upon by the medical profession as guidance for the treatment of diseases and disorders. Additional useful agents see also Physician's Desk Reference, 59.sup.th edition, (2005), Thomson P D R, Montvale N.J.; Gennaro et al., Eds. Remington's The Science and Practice of Pharmacy 20th edition, (2000), Lippincott Williams and Wilkins, Baltimore Md.; Braunwald et al., Eds. Harrison's Principles of Internal Medicine, 15.sup.th edition, (2001), McGraw Hill, NY; Berkow et al., Eds. The Merck Manual of Diagnosis and Therapy, (1992). Merck Research Laboratories, Rahway N.J.

V. Diagnostic Applications

Any of the anti-sADAM9v2 antibodies disclosed herein can also be used for detecting presence of sADAM9v2 (e.g., secreted sADAM9v2) in vitro or in vivo. Results obtained from such detection methods can be used for diagnostic purposes (e.g., diagnosing diseases associated with secreted sADAM9v2) or for scientific research purposes (e.g., identifying new sADAM9v2 secreting cell types, studying bioactivity and/or regulation of secreted sADAM9v2). For assay uses such as diagnostic uses, an anti-sADAM9v2 antibody as described herein may be conjugated with a detectable label (e.g., an imaging agent such as a contrast agent) for detecting presence of sADAM9v2 (e.g., secreted sADAM9v2), either in vivo or in vitro. As used herein, "conjugated" or "attached" means two entities are associated, preferably with sufficient affinity that the therapeutic/diagnostic benefit of the association between the two entities is realized. The association between the two entities can be either direct or via a linker, such as a polymer linker.

Conjugated or attached can include covalent or noncovalent bonding as well as other forms of association, such as entrapment, e.g., of one entity on or within the other, or of either or both entities on or within a third entity, such as a micelle.

In one example, an anti-sADAM9v2 antibody as described herein can be attached to a detectable label, which is a compound that is capable of releasing a detectable signal, either directly or indirectly, such that the aptamer can be detected, measured, and/or qualified, in vitro or in vivo. Examples of such "detectable labels" are intended to include, but are not limited to, fluorescent labels, chemiluminescent labels, colorimetric labels, enzymatic markers, radioactive isotopes, and affinity tags such as biotin. Such labels can be conjugated to the aptamer, directly or indirectly, by conventional methods.

In some embodiments, the detectable label is an agent suitable for detecting sADAM9v2 secreting cells in vitro, which can be a radioactive molecule, a radiopharmaceutical, or an iron oxide particle. Radioactive molecules suitable for in vivo imaging include, but are not limited to, $^{122}$I, $^{123}$I, $^{124}$I, $^{125}$I, $^{131}$I, $^{18}$F, $^{75}$Br, $^{76}$Br, $^{77}$Br, $^{211}$At, $^{225}$Ac, $^{177}$Lu, $^{153}$Sm, $^{186}$Re $^{188}$Re, $^{67}$Cu, $^{213}$Bi, $^{212}$Bi, $^{212}$Pb, and $^{67}$Ga, Exemplary radiopharmaceuticals suitable for in vivo imaging include $^{111}$In Oxyquinoline, $^{131}$I Sodium iodide, $^{99}$mTc Mebrofenin, and $^{99}$mTc Red Blood Cells, $^{123}$I Sodium iodide, $^{99}$mTc Exametazime, $^{99}$mTc Macroaggregate Albumin, $^{99}$mTc Medronate, $^{99}$mTc Mertiatide, $^{99}$mTc Oxidronate, $^{99}$mTc Pentetate, $^{99}$mTc Pertechnetate, $^{99}$mTc Sestamibi, $^{99}$mTc Sulfur Colloid, $^{99}$mTc Tetrofosmin, Thallium-201, or Xenon-133.

The reporting agent can also be a dye, e.g., a fluorophore, which is useful in detecting a disease mediated by sADAM9v2 secreting cells in tissue samples.

To perform a diagnostic assay in vitro, an anti-sADAM9v2 antibody can be brought in contact with a sample suspected of containing sADAM9v2, e.g., sADAM9v2 secreting cells or soluble sADAM9v2 in disease microenvironment. The antibody and the sample may be incubated under suitable conditions for a suitable period to allow for binding of the antibody to the sADAM9v2 antigen. Such an interaction can then be detected via routine methods, e.g., ELISA, histological staining or FACS.

To perform a diagnostic assay in vivo, a suitable amount of anti-sADAM9v2 antibodies, conjugated with a label (e.g., an imaging agent or a contrast agent), can be administered to a subject in need of the examination. Presence of the labeled antibody can be detected based on the signal released from the label by routine methods.

To perform scientific research assays, an anti-sADAM9v2 antibody can be used to study bioactivity of sADAM9v2, detect the presence of sADAM9v2 intracellularly, and or regulating the effect of secreted sADAM9v2. For example, a suitable amount of anti-sADAM9v2 can be brought in contact with a sample (e.g. a new cell type that is not previously identified as sADAM9v2 producing cells) suspected of producing sADAM9v2. The cells are permeabilized prior to contacting the anti-sADAM9v2 antibody. The antibody and the sample may be incubated under suitable conditions for a suitable period to allow for binding of the antibody to the sADAM9v2 antigen. Such an interaction can then be detected via routine methods, e.g., ELISA, histological staining or FACS.

VI. Kits for Therapeutic and Diagnostic Applications

The present disclosure also provides kits for the therapeutic or diagnostic applications as disclosed herein. Such kits can include one or more containers comprising an anti-sADAM9v2 antibody, e.g., any of those described herein.

In some embodiments, the kit can comprise instructions for use in accordance with any of the methods described herein. The included instructions can comprise a description of administration of the anti-sADAM9v2 antibody to treat, delay the onset, or alleviate a target disease as those described herein. The kit may further comprise a description of selecting an individual suitable for treatment based on identifying whether that individual has the target disease. In still other embodiments, the instructions comprise a description of administering an antibody to an individual at risk of the target disease.

The instructions relating to the use of an anti-sADAM9v2 antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder treatable by modulating immune responses, such as autoimmune diseases. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like.

Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-sADAM9v2 antibody as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

Also provided herein are kits for use in detecting secreted sADAM9v2 in a sample. Such a kit may comprise any of the anti-sADAM9v2 antibodies described herein. In some instances, the anti-sADAM9v2 antibody can be conjugated with a detectable label as those described herein. As used herein, "conjugated" or "attached" means two entities are associated, preferably with sufficient affinity that the therapeutic/diagnostic benefit of the association between the two entities is realized. The association between the two entities can be either direct or via a linker, such as a polymer linker. Conjugated or attached can include covalent or noncovalent bonding as well as other forms of association, such as entrapment, e.g., of one entity on or within the other, or of either or both entities on or within a third entity, such as a micelle.

Alternatively or in addition, the kit may comprise a secondary antibody capable of binding to anti-sADAM9v2 antibody. The kit may further comprise instructions for using the anti-sADAM9v2 antibody for detecting secreted sADAM9v2.

VII. General Techniques

The practice of the present invention will employ, unless otherwise indicated, conventional techniques of molecular biology (including recombinant techniques), microbiology, cell biology, biochemistry and immunology, which are within the skill of the art. Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever All publications cited herein are incorporated by reference for the purposes or subject matter referenced herein.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Discover of sADAM9v2

In the PCR analysis assessing ADAM9 expression, discrepancies were observed in the lengths of some ADAM9 sequences when compared to the predetermined benchmark (refer to FIG. 1, denoted by the red arrow). This research endeavor sought to authenticate the expression of the ADAM9 gene in various prostate cancer cell lines and control samples. These comprised NC (a Negative Control signifying an absence of prostate cancer sample), PC (representing the ADAM9 gene as a positive control), BPH-1 (Benign Prostate Hyperplasia-1), LNCaP (a prostate cancer cell line derived from a patient with lymph node metastasis), C4-2 (an androgen-insensitive derivative of LNCaP), C4-2B (indicative of the bone metastasis propensity of C4-2), CWR22Rv1 (a prostate cancer cell line symbolizing androgen mutation), DU145 (a prostate cancer cell line sourced from a patient manifesting brain metastasis), PC3 (a prostate cancer cell line extracted from a patient exhibiting bone metastasis), and PC3M (cell derivatives from PC3 displaying pronounced metastatic behavior in a mice model). The focal objective of this investigation was to ascertain the expression of ADAM9 mRNA in the aforementioned prostate cancer cell lines. RNA was isolated utilizing the Qiagen RNA isolation system (supplied by Qiagen, Inc.) and subsequently transformed to cDNA via the MMLV reverse transcriptase system. The PCR procedure was facilitated by introducing cDNA into a PCR reagent (provided by ThermoFisher, Inc.) and performing PCR analysis through agarose gel electrophoresis. The findings elucidated that these cell lines not only housed the complete ADAM9 mRNA sequence but also diverse variants. The results underscore the potential of ADAM9 messenger RNA to exhibit distinct alternative splicing iterations in prostate cancer cells, which may be instrumental in the malignancy and metastatic progression of prostate cancer. Therefore, we isolate these PCR bands to perform gene sequences.

Figure 2:
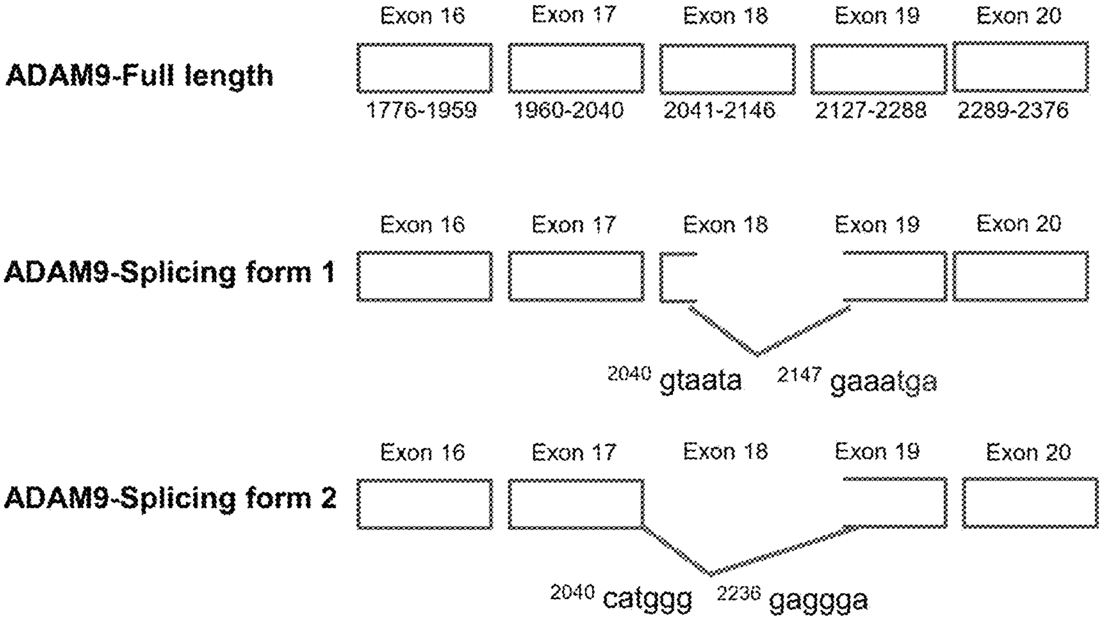
FIG. 2 shows the outcomes of the comprehensive sequencing illustration of ADAM9 gene, revealing the presence of alternative splicing variants. While the ADAM9 variant 1 has been previously documented, the data also indicates the expression of the novel ADAM9 variant 2, which has not been delineated in any prior reports.

Illustration of ADAM9 genes after ADAM9 full gene sequencing, we found that there is an alternative splicing variant (see FIG. 2). Please be aware that the ADAM9-Splicing form 1 exhibits alternative splicing between positions 2046 in exon 18 and 2147 in exon 19. This leads to out-of-frame splicing and an early termination of ADAM9 translation. Consequently, there is a loss of the transmembrane and cytoplasmic domains of the full-length ADAM9. Additionally, we identified a novel alternative splicing event that demonstrates a loss between positions 2040 in exon 18 and 2236 in exon 19. This results in the omission of the transmembrane domain, yet the cytoplasmic sequence remains in-frame.

Figure 3:
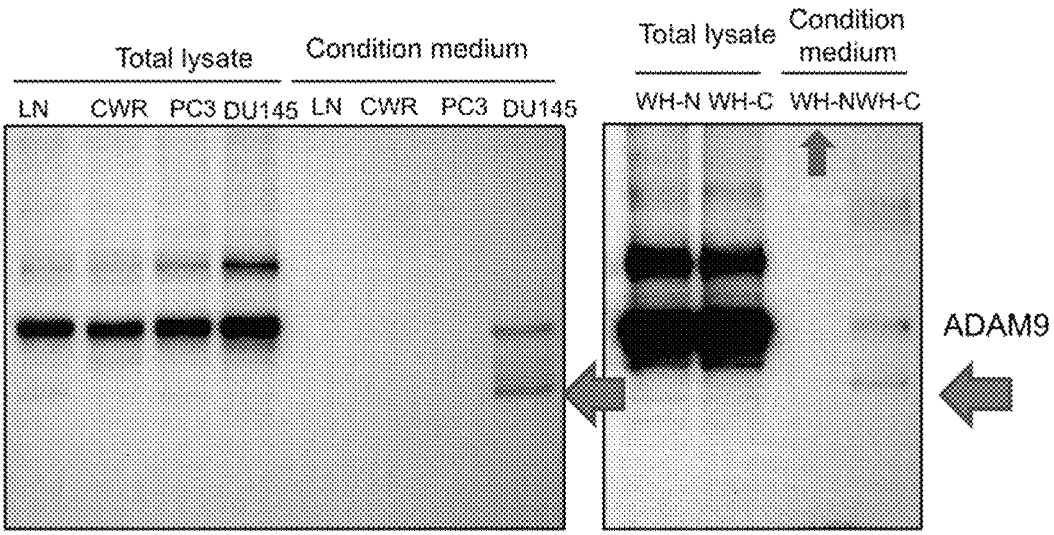
FIG. 3 depicts the identification of sADAM9 exclusively in the tumor cells and adjacent periphery cells of the carcinoma. This illustration provides a protein expression analysis of ADAM9 in LN (LNCaP), CWR (CWR22rv1), PC3, and DU145, sourced from both the total cell lysate and protein isolates from cultured medium (conditioned medium). Additionally, cells from benign (WHN) and tumor (WHC) regions of a prostate cancer patient were procured to authenticate whether sADAM9 is secreted by tumor-associated peripheral cells.

Further examination of the cultured medium from tumor, tumor-associated periphery cells, and normal tissue revealed that sADAM9 was exclusively detected in the medium from tumor and tumor-associated periphery cells (see FIG. 3). Prior to collecting the medium, cells were cultured for a duration of three days, after which proteins in the medium were concentrated. Concurrently, cultured cells were collected, and protein extraction was performed using the protein extraction system (RIPA buffer, which includes NaCl 150 mM, Triton-X-100 1%, sodium deoxycholate 0.5%, SDS 0.1%, and Tris-HCL pH8.0 50 mM). This study aimed to validate the expression of the ADAM9 gene across various prostate cancer cell lines and corresponding control samples. This set included NC (a control indicating no prostate cancer sample presence), PC (acting as a positive control for the ADAM9 gene), BPH-1 (Benign Prostate Hyperplasia-1), LNCaP (a prostate cancer cell line sourced from a patient displaying lymph node metastasis), C4-2 (an androgen-insensitive offshoot of LNCaP), C4-2B (showcasing the bone metastasis tendency of C4-2), CWR22Rv1 (a prostate cancer cell line representing androgen mutation), DU 145 (a prostate cancer cell line derived from a patient with brain metastasis), PC3 (a prostate cancer cell line obtained from a patient evidencing bone metastasis), and PC3M (cell strains from PC3 exhibiting significant metastatic tendencies in a mouse model). For the protein analysis, a standard Western Blotting procedure utilizing an 8% polyacrylamide gel was implemented. Proteins were transferred from the gel to a nitrocellulose membrane via electrophoresis. For the Western Blotting analyses, specific antibodies from R&D Biosystem, particularly for ADAM9 (MAB939), were employed.

Figure 4:
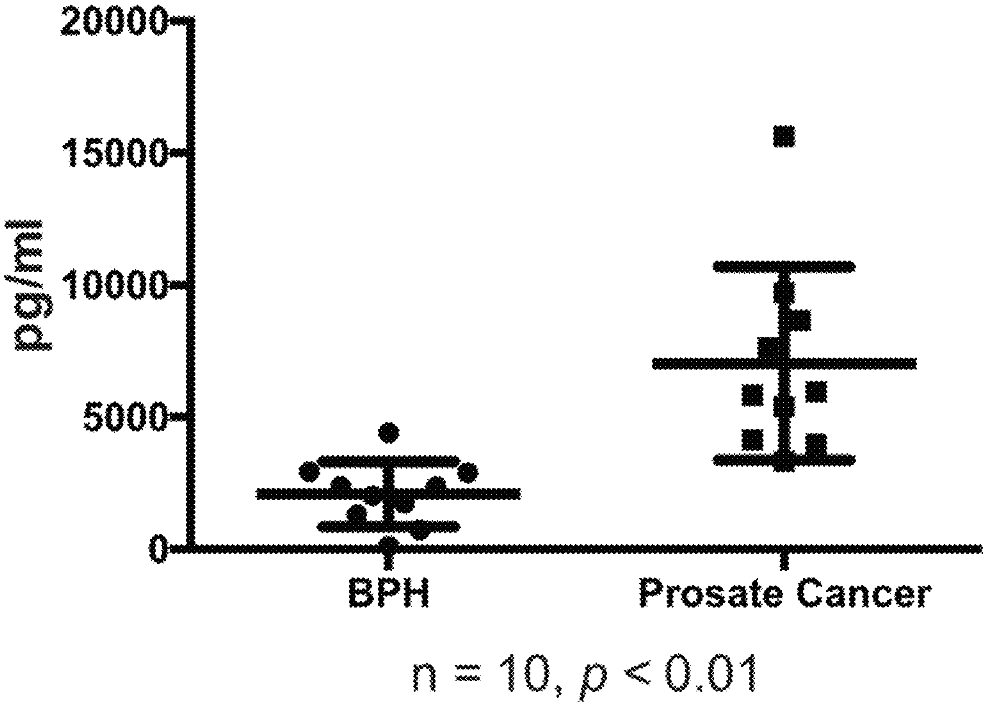
FIG. 4 shows the expression of sADAM9 in the blood of cancer patients was significantly increased when using ELISA to detect the expression of ADAM9 in the blood of benign prostatic hyperplasia (BPH) and prostate cancer patients.

In a particular embodiment, an ELISA system is utilized to perform blood test to assess the expression of sADAM9 in patients with benign prostatic hyperplasia (BPH) and prostate cancer. As illustrated in FIG. 4, the expression of sADAM9 in prostate cancer patients is markedly higher compared to BPH patients. Serum samples from BPH and prostate cancer patients were procured, with the identities anonymized, from the Taipei Medical University (TMU) Biobank, encompassing 10 samples each from BPH and prostate cancer patients. The ELISA analysis was executed in adherence to the standard protocols provided by R&D Biosystems, Inc., and the corresponding ELISA kit (DY939) was acquired from the same enterprise.

Figure 5:
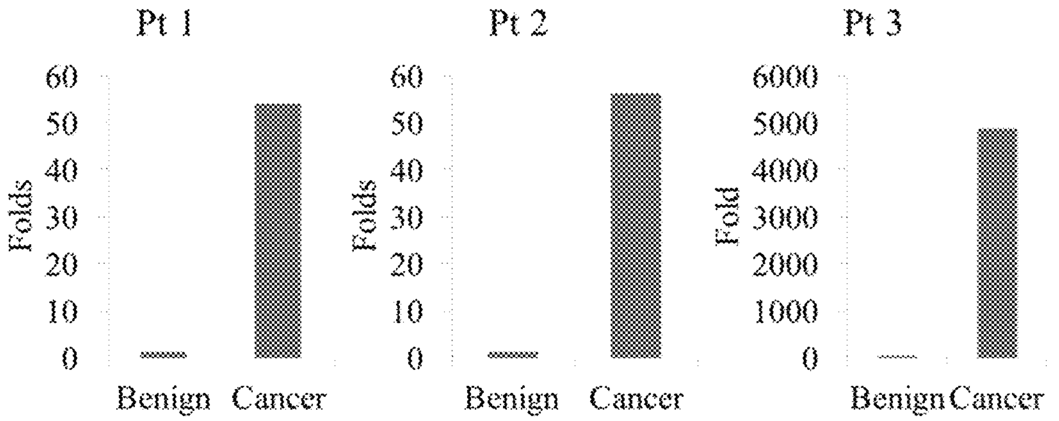
FIG. 5 shows the sADAM9v2 expression at cancer cells and benign cells in 3 patients isolated by laser capture microdissection (LCM).

As depicted in FIG. 5, the expression of sADAM9v2 in cancerous associated peripheral cells surpasses that in benign counterpart of same patient, as determined from 3 patients using Laser Capture Microdissection (LCM). To ascertain that sADAM9v2 is predominantly expressed in prostate tumor-associated peripheral cells, LCM was employed on tissue samples from three distinct patients. These tissue slides, sourced from TMU Biobank, had their tumor and peripheral regions validated by a pathologist. LCM procedures were adhered to as per the guidelines of the commercial kit (Arcturus® Kit for DNA and RNA Extraction and purification, Invitrogen, Inc.). The LCM operations were facilitated using the MMI CellCut and Cell Ector systems, available at the TMU core facility. Subsequently, RNA from these cells was isolated using the Arcturus® PicoPure® Frozen RNA isolation Kit, and cDNA was synthesized with the MMLV cDNA system (Thermo Fisher Scientific, Inc.). Quantitative PCR analyses were executed on the LightCycler® 480 System (Roche Diagnostics, Inc.). The fold differences were calculated using the 2^delta-delta CT analysis method, as outlined by NIH (published in Biostat. Bioinforma Biomath. 2013 August; 3(3): 71-85). The final results were expressed in terms of fold changes, derived by comparing cancerous to benign results.

Figure 6:
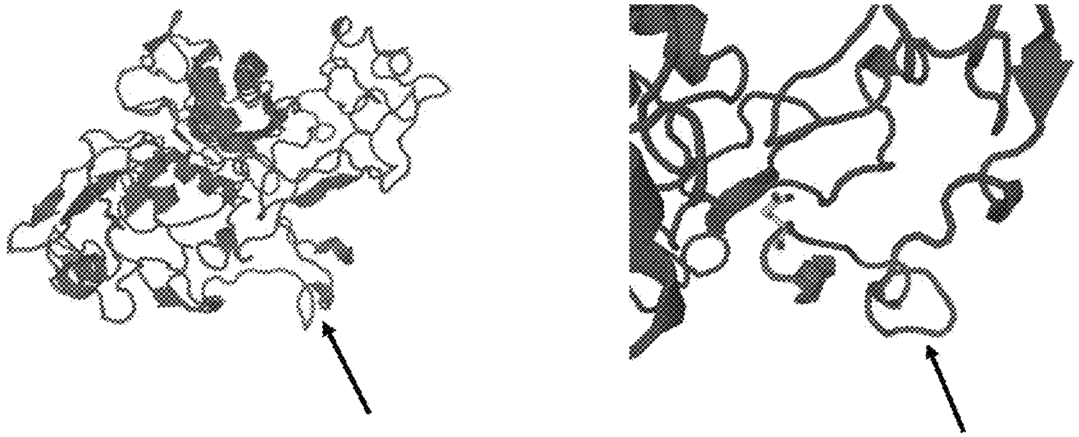
FIG. 6 shows that the alternative splicing sites are highly antigenic according to the computation model.

According to these tests, it is confirmed that sADAM9v2 is expressed in the tumor cell and the periphery cells. This disclosure performs a structure simulation of ADAM9v2 and find out that the alternative splicing sites are highly antigenic, as indicated by the arrows (see FIG. 6).

Figure 7:
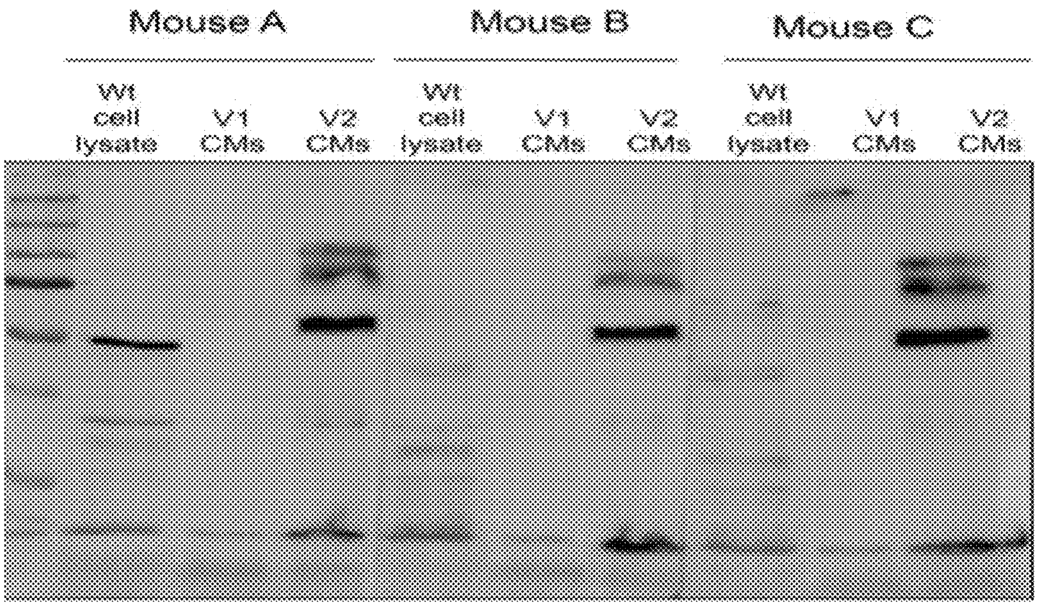
FIG. 7 shows the result of hybridoma analysis against sADAM9v2.

Herein after, the present disclosure performs a test for the specificity of sADAM9v2 with hybridoma. Cell lysate and conditioned mediums (CMs) for sADAM9v1 and sADAM9v2 are also collected to test the specificity of the antibody. The result is showed in FIG. 7. We select the antibody of mouse that generated mAb of ADA M9 to perform the following examination. For the generation of the sADAM9v2 hybridoma and mAb, the NMRI mouse strain was employed. All animal procedures adhered to the recommended national and international standards for animal care and handling. Initial steps involved preparing immunoconjugates following conventional coupling procedures using N-3-dimethylaminopropyl)-N-ethylcarbodiimide (EDC). The peptide and its carrier (bovine serum albumin) were combined in equal proportions and suspended in phosphate-buffered saline (PBS) supplemented with 50 mM $NaHCO_3$ buffer. We selected NMRI mice aged between 6 to 12 weeks for immunization, administering 150 micrograms of the immunoconjugate in 200 microliters of PBS, combined with 100 microliters of complete Freund's adjuvant. A booster shot, featuring the identical quantity of the immunoconjugate, was administered after 6 weeks. Blood samples were drawn in the 7th week post-initial injection. For hybridoma development, murine SP2/0 cells were utilized. These cells were cultured in a solution containing 10 mL RPMI-1640, 10% FBS, and 2 mM L-glutamine (5 mL). After the 7th week of immunization, mice were euthanized, and a spleen cell suspension was prepared. This was subsequently suspended in a balanced salt buffer (BSS)—composed of 125 mM NaCl, 5 mM KCl, 4 mM $CaCl_2$), 2.5 mM $MgCl_2$, and 5 mM Tris-HCl at pH 7.4. The mixture was then combined with PEG8000, and electroporation was facilitated by balancing the ratio of splenocytes to myeloma cells, which were later suspended in HAT medium for a week. Upon stabilizing the cultured cells, hybridoma cloning was executed. We ultimately identified a monoclonal hybridoma that was confirmed to produce an mAb with marked specificity towards ADAM9v2.

Preparation of Recombinant Human sADAM9v2 mAb: After identifying the distinct hybridoma suitable for producing the sADAM9v2 mAb, we conducted isotype assessment and categorization to determine the unique isotype of the sADAM9v2 mAb present within the hybridoma. The isotype screening was facilitated using the hybridoma isotyping ELISA system sourced from Thermo Fisher. With the isotype duly verified, a sequencing analysis was carried out on the specific antibody isotype present in the hybridoma. After verifying the distinct sequences for both the heavy and light chains, we proceeded to isolate and clone the specific sequences pertaining to the sADAM9v2 mAb. This was achieved by PCR targeting the specified sequences, which were then integrated into the TGEX-Heavy Chain and TGEX-Light Chain expression vectors for subsequent applications. The TGEX vector housing the heavy and light chains of sADAM9v2 mAb ensures a consistent and preserved expression of our patented antibody within our system.

Migration of prostate cancer cell according to sADAM9: The Transwell cell migration assay, utilizing the Corning® System, was employed to assess the movement of prostate cancer cells following the introduction of sADAM9. We procured the recombinant ADAM9 (rADAM9) from R&D Biosystems® for addition to the transwell setup. The observed data revealed that sADAM9 (in the form of rADAM9) prompts prostate cancer cell migration in a manner proportional to the dose (as depicted in the figure on the left). Furthermore, the including the mAb for sADAM9v2 inhibited cell migratory activity within the transwell system, suggesting that the sADAM9v2 mAb functions as a neutralizing antibody (mAb).

Figure 8:
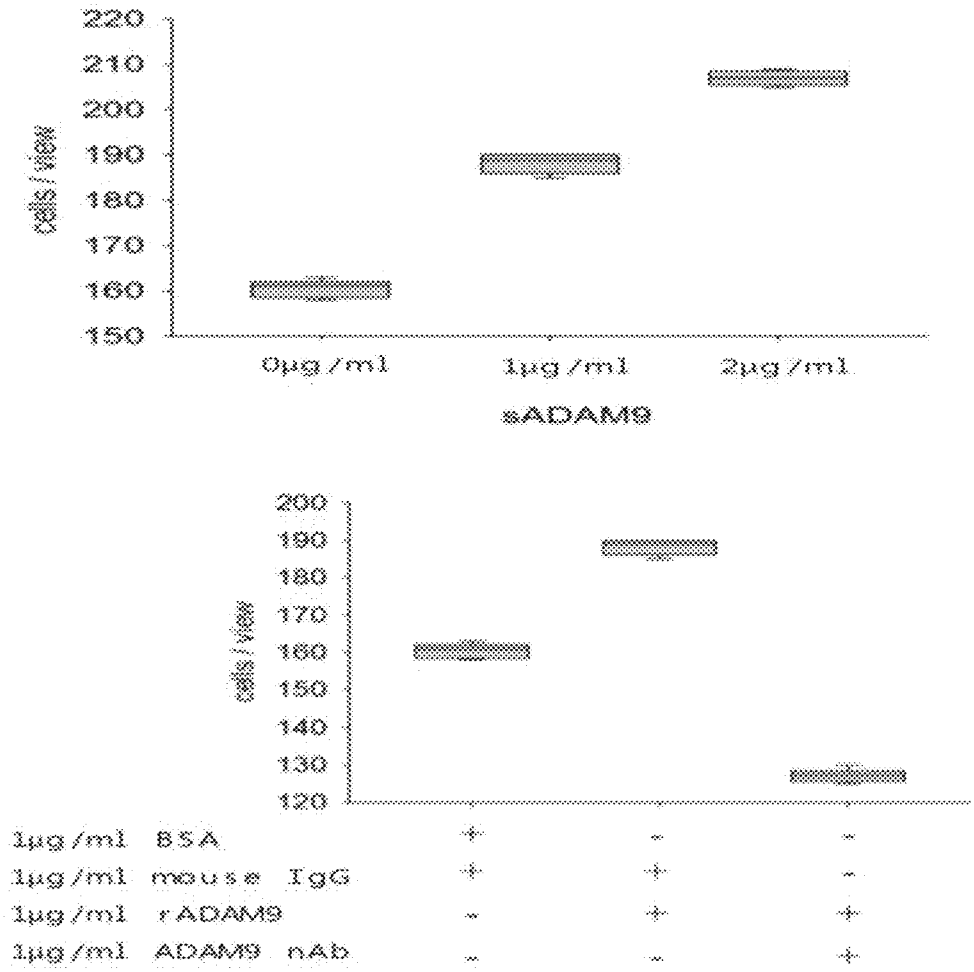
FIG. 8 shows that sADAM9v2 improves the dose-dependent migration of prostate cancer cells in transwell, which can be inhibited by sADAM9v2 mAb.

The result is showed as FIG. 8, the mobility of prostate cancer cell is dose dependent to the concentration of sADAM9, and the developed sADAM9v2 mAb may decrease the mobility of prostate cancer cell.

Our prior findings underscored the specificity of the sADAM9v2 mAb and its role in curtailing the motility of prostate cancer cells. It's well-documented that the migratory and invasive behaviors of prostate cancer cells are linked to the downstream cell regulation of AKT and Src. Consequently, we conducted studies on the AKT (cited: Int. J. Mol. Sci., 2020 June; 21(12): 4507) and Src pathways (cited: Cancer and Metastasis Reviews 2014 February; 33: 595-606). Therefore, following above test, the present disclosure further try to find out the mechanism of sADAM9 for increasing the movement and migration of prostate cancer, and find out that sADAM9 activates the downstream effectors of AKT to increase the movement and migration of prostate cancer. The protein assays revealed an elevated level of AKT phosphorylation. Prostate cancer cells were grown either on plates coated with collagen-1 (given the abundance of collagen in bones) or without. Before harvesting, cells were treated with 5 μg/ml of sADAM9 for intervals of 30 or 60 minutes. Cell lysis was carried out using a protein lysis buffer (RIPA Buffer) supplemented with a phosphatase inhibitor. The activity of AKT and Src was validated by assessing the phosphorylation levels of AKT and Src using antibodies specifically targeting the phosphorylated forms of AKT and Src, obtained from Cell Signaling®.

Figure 9:
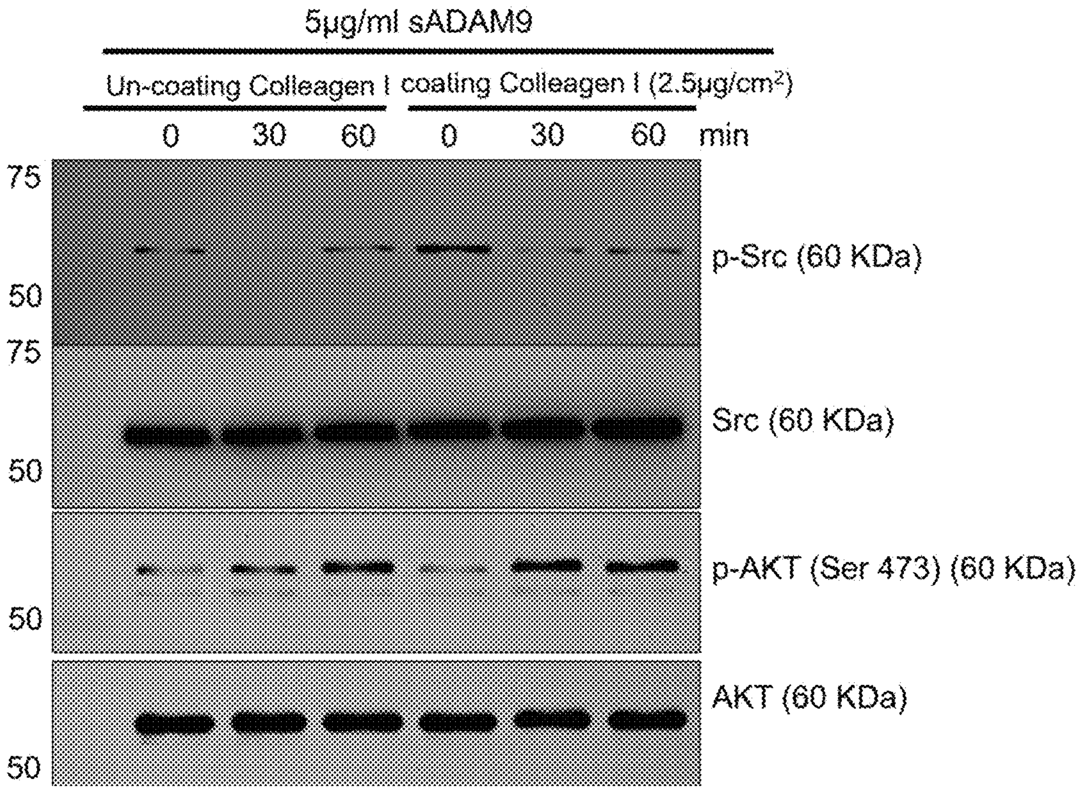
FIG. 9 shows the migration and metastasis of prostate cancer cells induced by the downstream signal of AKT activated by sADAM9.

As showed in FIG. 9, sADAM9 has the ability to enhance cell motility downstream signals, such as AKT phosphorylation. In addition, sADAM9v2 mAb block cell motility as showed in FIG. 8. Therefore, we hypothesize that the sADAM9v2 mAb block prostate cancer motility through the inhibition of AKT phosphorylation.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or"

should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A): in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A. and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

The above mentioned amino acid sequence list is show in Table 1 as follow.

TABLE 1

| SEQ ID | Residues |
|---|---|
| (SEQ ID NO: 1) | GYTFTSYD |
| (SEQ ID NO: 2) | IYPRDGST |
| (SEQ ID NO: 3) | ARWGGDH |
| (SEQ ID NO: 4) | QSLLNSRTRK NY |
| (SEQ ID NO: 5) | WAS |
| (SEQ ID NO: 6) | KQSYIL WT |
| (SEQ ID NO: 7) | VQLEQSGPEL VKPGASVKLS CKASGYTFTS YDINWVRQRP GQGLEWIGWI YPRDGSTTFN EKFRGKARLT VDTSSSTAYM ELHSLTSEDS AVYFCARWGG DH |
| (SEQ ID NO: 8) | VLTQSPSSLA VSAGEKVTMS CKSSQSLLNS RTRKNYLAWY QQKPGQSPKR LIYWASTRES GVPDRFTGSG SGTDFTLTIS SVQTEDLAVY YCKQSYILWT |
| (SEQ ID NO: 9) | DVQLEQSGPE LVKPGASVKL SCKASGYTFT SYDINWVRQR PGQGLEWIGW IYPRDGSTTF NEKFRGKARL TVDTSSSTAY MELHSLTSED SAVYFCARWG GDHWGQGTTL TVSS |
| (SEQ ID NO: 10) | SSELVLTQSP SSLAVSAGEK VTMSCKSSQS LLNSRTRKNY LAWYQQKPGQ SPKRLIYWAS TRESGVPDRF TGSGSGTDFT LTISSVQTED LAVYYCKQSY ILWTFGGGTK LEIK |

What is claimed is:

1. An antibody or antigen-binding fragment thereof, which binds to a sADAM9v2 protein or a partial peptide thereof, wherein the antibody or antigen-binding fragment thereof comprises:
   - a heavy chain comprising
     - CDR1 comprising the amino acid sequence of SEQ ID NO: 1,
     - CDR2 comprising the amino acid sequence of SEQ ID NO: 2, and
     - CDR3 comprising the amino acid sequence of SEQ ID NO: 3; and
   - a light chain comprising
     - CDR1 comprising the amino acid sequence of SEQ ID NO: 4,
     - CDR2 comprising the amino acid sequence of SEQ ID NO: 5, and
     - CDR3 comprising the amino acid sequence of SEQ ID NO: 6.

2. The antibody or antigen-binding fragment thereof of claim 1, comprising
   - a heavy chain variable region comprising the amino acid sequence having at least 90% identity to SEQ ID NO: 7; and
   - a light chain variable region comprising the amino acid sequence at least 90% identity to SEQ ID NO: 8.

3. The antibody or antigen-binding fragment thereof of claim 1, wherein the heavy chain comprising the amino acid sequence having at least 90% identity to SEQ ID NO: 9.

4. The antibody or antigen-binding fragment thereof of claim 1, wherein the light chain comprising the amino acid sequence having at least 90% identity to SEQ ID NO: 10.

5. The antibody or antigen-binding fragment thereof of claim 1, which is conjugated with a therapeutic agent, fluorescent labels, chemiluminescent labels, colorimetric labels, enzymatic markers, radioactive isotopes, and affinity tags.

6. A polynucleotide encoding the antibody or antigen-binding fragment thereof of claim 1.

7. A reagent for predicting or diagnosing a sADAM9v2-related disease, determining drug efficacy after treatment with a sADAM9v2 inhibitor, or screening for a subject in whom treatment with a sADAM9v2 inhibitor is highly effective, wherein the reagent comprises the antibody or antigen-binding fragment thereof of claim 1.

8. A method for predicting or diagnosing a sADAM9v2-related disease or a predisposition for developing the sADAM9v2-related disease in a subject, wherein the method comprises the steps of:

(a) contacting a sample isolated from the subject with the antibody or antigen-binding fragment thereof of claim 1;

(b) detecting a sADAM9v2 protein in the sample by detecting binding between the antibody or antigen-binding fragment thereof and the sample; and (c) comparing the level of the sADAM9v2 protein in the sample to a control, wherein a higher sADAM9v2 protein level than the control indicates that the subject suffers from the disease or has a risk of developing the disease.

9. The method of claim 8, wherein the sADAM9v2-related disease is a cancer expressing sADAM9v2.

10. The method of claim 9, wherein the cancer is prostate cancer.

11. A method for treating sADAM9v2-related disease in a subject, comprising administering to the subject an effective amount of the antibody or antigen-binding fragment thereof of claim 1.

12. A pharmaceutical composition, comprising an effective dose of an antibody or antigen-binding fragment thereof of claim 1 and a pharmaceutically acceptable carrier.

* * * * *